(12) United States Patent
Quirk et al.

(10) Patent No.: US 7,384,598 B2
(45) Date of Patent: Jun. 10, 2008

(54) DIAGNOSTIC DEVICE

(75) Inventors: Stephen Quirk, Alpharetta, GA (US); Robert John Lyng, Alpharetta, GA (US); Rosann Marie Kaylor, Cumming, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 457 days.

(21) Appl. No.: 10/026,610

(22) Filed: Dec. 21, 2001

(65) Prior Publication Data

US 2003/0118479 A1     Jun. 26, 2003

(51) Int. Cl.
  G01N 21/00    (2006.01)
  G01N 21/03    (2006.01)
  G01N 33/558   (2006.01)
(52) U.S. Cl. .................. 422/58; 436/165; 436/514
(58) Field of Classification Search ............ 422/55–58, 422/82.05, 82.08, 82.09, 100, 101
  See application file for complete search history.

(56) References Cited

U.S. PATENT DOCUMENTS

| | | | |
|---|---|---|---|
| 4,151,832 A | 5/1979 | Hamer | |
| 4,761,381 A | 8/1988 | Blatt et al. | |
| 4,992,385 A | 2/1991 | Godfrey | |
| 5,196,350 A | 3/1993 | Backman et al. | |
| 5,221,579 A | 6/1993 | Kwiatek et al. | |
| 5,677,133 A * | 10/1997 | Oberhardt | 435/7.1 |
| 5,800,779 A * | 9/1998 | Johnson | 422/58 |
| 5,922,550 A | 7/1999 | Everhart et al. | |
| 6,020,047 A | 2/2000 | Everhart | |
| 6,048,623 A | 4/2000 | Everhart et al. | |
| 6,060,256 A | 5/2000 | Everhart et al. | |
| 6,099,484 A | 8/2000 | Douglas et al. | |
| 6,153,439 A | 11/2000 | Johnson | |
| 6,180,288 B1 | 1/2001 | Everhart et al. | |
| 6,184,029 B1 * | 2/2001 | Wilding et al. | 435/287.1 |
| 6,261,519 B1 | 7/2001 | Harding et al. | |
| 6,686,208 B2 * | 2/2004 | Meusel et al. | 436/518 |

FOREIGN PATENT DOCUMENTS

| | | |
|---|---|---|
| EP | 0312394 A2 | 4/1989 |
| GB | 2332943 A | 7/1999 |
| WO | 94/13835 | 6/1994 |
| WO | WO 97/03347 | 1/1997 |
| WO | 98/27417 | 6/1998 |
| WO | WO 9843086 A1 | 10/1998 |
| WO | WO 9931486 A1 | 6/1999 |
| WO | WO 00/36416 | 6/2000 |
| WO | WO 0034781 A2 | 6/2000 |
| WO | WO 0034781 A3 | 6/2000 |
| WO | WOO 0036416 A1 | 6/2000 |
| WO | WO 00/50891 | 8/2000 |

* cited by examiner

Primary Examiner—Jill Warden
Assistant Examiner—Lore Ramillano
(74) Attorney, Agent, or Firm—Dority & Manning, P.A.

(57) ABSTRACT

Diagnostic devices for detecting the presence of an analyte in a sample are provided. Devices of the present invention comprise a means for inducing a pressure differential on a sample to direct the sample to a test surface. In one embodiment, the means for inducing a pressure differential on a sample to direct the sample to a test surface comprises a syringe that can be used to draw a sample from an opening to a test surface. In other embodiments, the device also provides means for diluting a sample. In yet other embodiments, the device also provides a means.

13 Claims, 3 Drawing Sheets

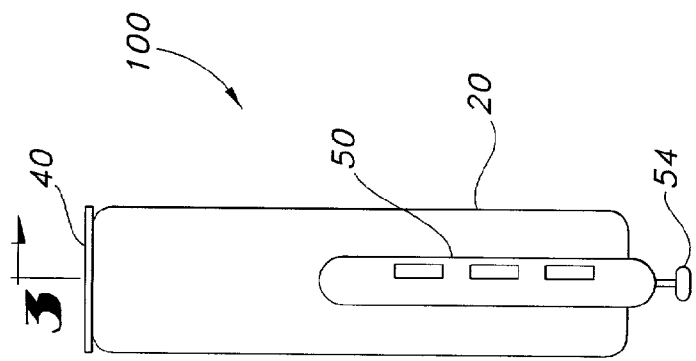
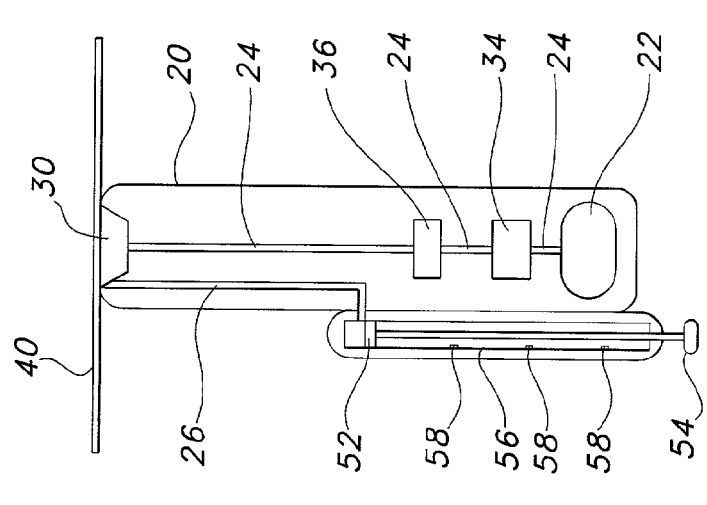
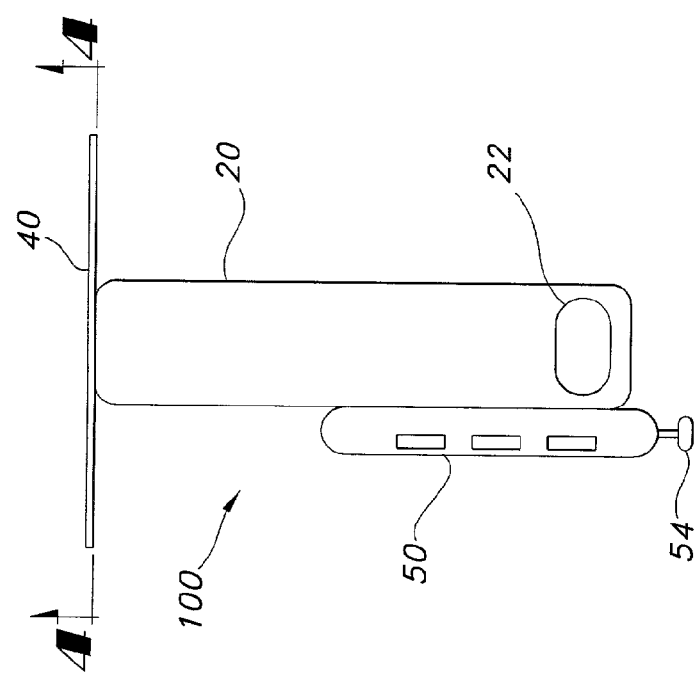
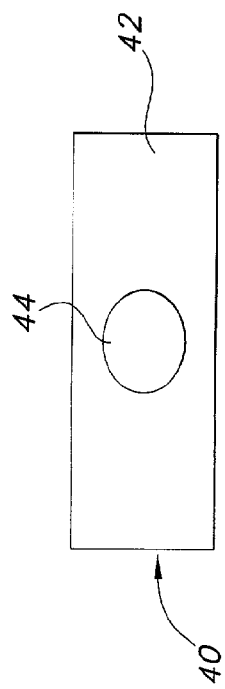

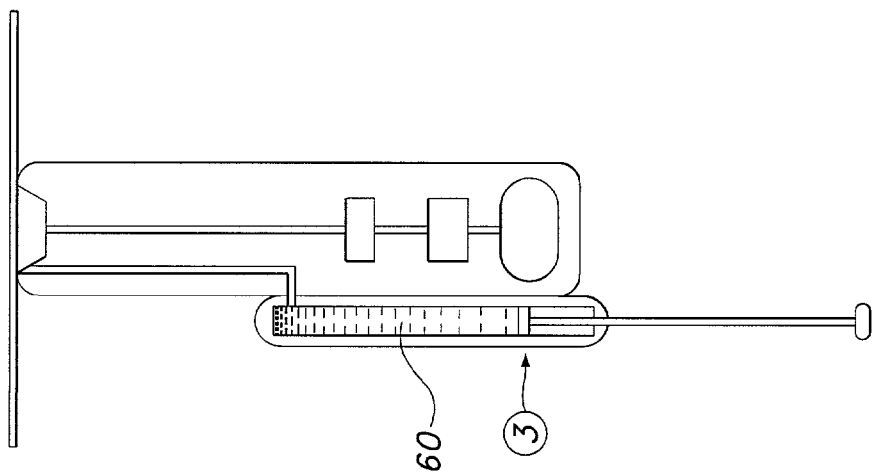
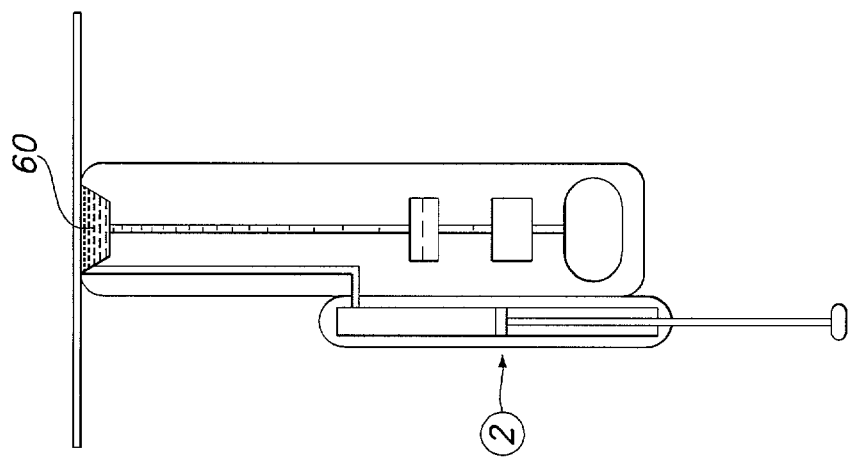
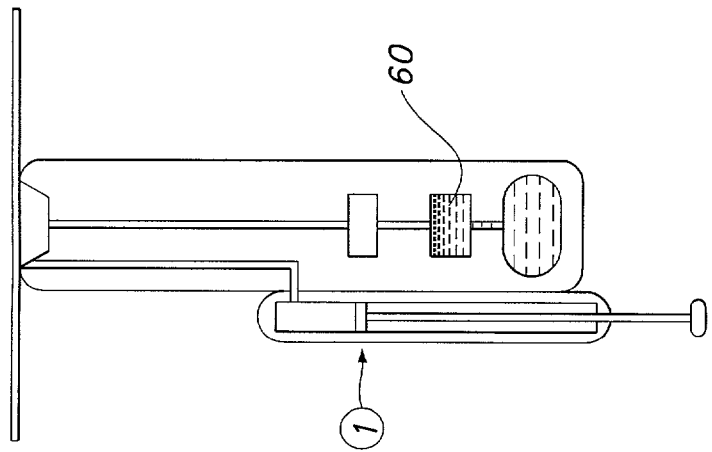

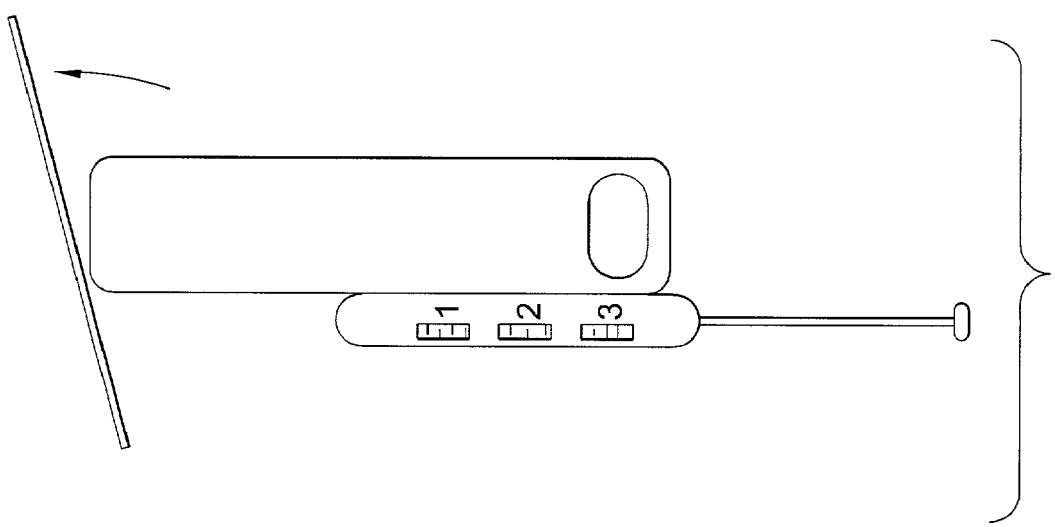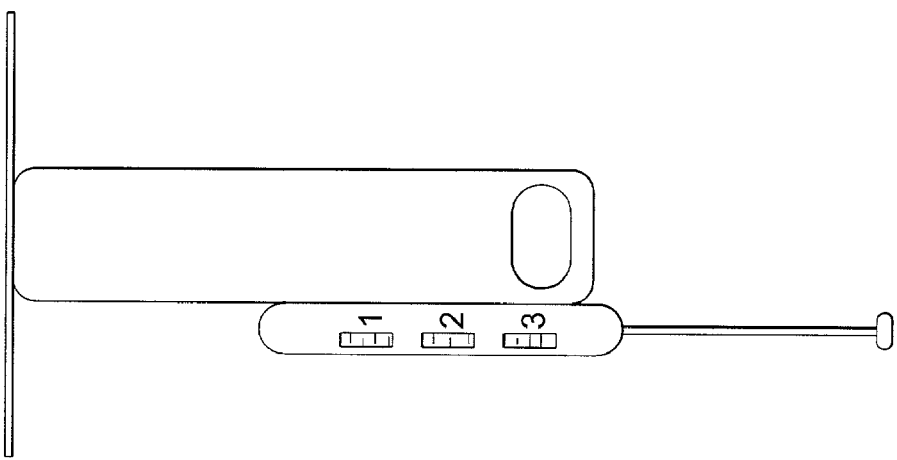

DIAGNOSTIC DEVICE

FIELD OF THE INVENTION

The present invention relates to diagnostic devices. Particularly, the present invention relates to devices that comprise a means for inducing a pressure differential on a sample to direct the sample to a test surface.

BACKGROUND

Diagnostic devices are used to detect an analyte in a sample. The present invention relates to diagnostic devices and methods. In one particular embodiment, the present invention relates to diffraction-based diagnostic devices that can be used to detect one or more analytes present in a medium by detecting diffraction of an analyte/binder complex. These diffraction-based devices comprise a surface upon which is printed in a pattern a binder. Upon attachment of analyte to the binder that is printed in a pattern on the surface, diffraction of light that is transmitted through or reflected off of the printed surface occurs via the physical dimensions and defined placement of the binder.

U.S. Pat. No. 4,992,385 to Godfrey, et al. describes a method of preparing a diffraction grating from a thin polymer film for subsequent use as a sensing device. The sensing device described in U.S. Pat. No. 4,992,385 requires the use of a spectrophotometric technique to detect changes in the device's optical properties due to analyte binding. The device and method described in U.S. Pat. No. 4,992,385 require a complex detection method to detect changes in the diffraction pattern because changes in a diffraction pattern are more subtle than the qualitative determination that is made to determine whether a diffraction image is formed or is not formed.

U.S. Pat. No. 5,196,350 to Backman et al. describes an optical detection method for detecting the presence of specific ligands. The method described in U.S. Pat. No. 5,196,350 is an optical detection method for detecting specific ligands that requires a mask comprising slits to produce a diffraction pattern. An immunoassay device is placed between the mask and light source, so that binding by an analyte causes a change in the diffraction or interference pattern caused by the mask. Again, this method also requires a complex detection method to detect changes in a diffraction pattern and confirm the presence of a ligand.

International Publication No. WO 94/13835 describes a method and a system to detect biological macromolecules via diffraction of light from a probe of predetermined dimensions that diffracts light in a known pattern. The probe comprises an active surface that is able to highly concentrate the macromolecules relative to their concentration in the sample solution. The method and the system described in WO 94/13835 also require the use of a complex detector and an analyzer in order to detect changes in the diffraction pattern produced by the probe.

U.S. Pat. No. 6,261,519 describes a diagnostic device for measuring the concentration of an analyte in a sample. The device comprises a sample port at one end for introducing a sample. The device also comprises a bladder at the other end that must be depressed, inserted into a liquid sample and released to draw a sample. The device described in U.S. Pat. No. 6,261,519 does not further draw the sample past a test site to clear the test site so that diffraction or non-diffraction at the test site can be determined.

The methods, systems and devices discussed above do not provide a means for directing a sample to a test surface and then clearing the test surface of sample so that diffraction or non-diffraction can be determined. Furthermore, the prior art fails to provide a device in which a user of the device can control the position of a sample with in the device. What is needed is a simple, easy to use method, system and device for detecting an analyte that provides a means for directing a sample to a test surface and then clears the test surface of enough sample so that diffraction, and binding, can be accurately determined and allows a user of the device to control movement and incubation or reaction time of a sample within the device.

SUMMARY OF THE INVENTION

The present invention provides diagnostic devices comprising a means for inducing a pressure differential on a sample to direct the sample to a test surface. In one embodiment, the means for inducing a pressure differential on a sample to direct the sample to a test surface comprises a syringe or a piston for pushing or pulling a fluid sample to the test surface. In one embodiment, the diagnostic device is a diffraction-based diagnostic device and the means for inducing a pressure differential on a sample to direct the sample to a test surface also further directs the sample past the test surface and removes most of the sample from the test surface so that the test surface can be observed by an individual or read by an analyzer. In a desirable embodiment, the test surface is located on a test strip that can be removed from the device and observed by an individual or inserted into an analyzer.

Features, aspects and advantages of the present invention will become better understood with reference to the following description and the appended claims. The accompanying drawings, which are incorporated in and constitute a part of this specification, illustrate several examples of the invention and, together with the description, serve to explain the principles of this invention.

BRIEF DESCRIPTION OF THE FIGURES

The invention is hereinafter more particularly described by way of examples with reference to the following drawings in which:

FIG. 1 is a top view of a diagnostic device that includes a pressure-assisted means for directing a sample to a test surface.

FIG. 2 is a side view of the diagnostic device.

FIG. 3 is a cross-sectional view of the diagnostic device taken through line 3-3 of FIG. 2.

FIG. 4 is a top view of a diagnostic test strip separated from the device.

FIGS. 5, 6 and 7 are cross-sectional views of the diagnostic device taken through line 3-3 of FIG. 2 in various stages of operation of the pressure-assisted means.

FIG. 8 is a top view of the diagnostic device after operating the pressure-assisted means.

FIG. 9 is a top view of the diagnostic device illustrating one mode of removal of a removable test strip.

FIG. 10 is a side view of the removed test strip.

Repeated use of reference characters in the present application and drawings is intended to represent the same, similar or analogous features or elements of the invention.

DETAILED DESCRIPTION

Although the present invention is described in the context of several specific examples, configurations and embodiments, it will be appreciated that further combinations or alterations of the examples, configurations and embodiments illustrated herein and described herein may be made by one skilled in the art without departing from the spirit and scope of the present invention. In addition, although reference is often made with respect to diffraction-based diagnostic devices, methods and systems for detecting a protein, those skilled in the art will appreciate that other modifications may be made to adapt the diagnostic devices, methods and systems for use with non-diffraction based diagnostic devices, methods and systems and for detecting analytes other than proteins. In the following discussion, reference is made to several figures to illustrate a few specific examples and embodiments of the present invention.

The present invention provides a diagnostic device that comprises a means for inducing a pressure differential on a sample to direct the sample to a test surface. The means for inducing a pressure differential on a sample to direct the sample to a test surface may direct all or a portion of the sample to the test surface. In addition, the means for inducing a pressure differential on a sample to direct the sample to a test surface also further directs the sample past the test surface to remove excess or unreacted sample from the test surface and may include additional means or structures to do so. Desirably, the sample is directed past the test surface after the sample or a portion of the sample has become bound, reacted or otherwise interacted with the test surface.

One embodiment of the present invention provides a device and method for directing a sample to a diffraction-based test surface and is described and illustrated herein. For example, a diffraction-based diagnostic device can be used to direct a liquid sample, such as blood, to a diffraction-based test surface that tests for one or more analytes such as a protein, such as C-reactive protein, IgE antibodies and so forth.

Examples of methods, systems and devices for detecting an analyte via the formation of a diffraction image are disclosed and described in U.S. Pat. Nos. 5,922,550, 6,020,047, 6,221,579 and International Publication No. WO 98/27417 which are hereby incorporated by reference herein in their entirety. The devices described in the above-referenced documents can be produced by printing a species onto a surface. The species is selected to bind, react or otherwise associate with an analyte of interest and is referred to herein as a "binder". A binder may include any chemical species, compound, composition, moiety, particle and so forth that will bind, react or otherwise associate with the analyte of interest. Preferably, the binder is specific to the analyte of interest or a class of analytes of interest and does not appreciably bind, react or otherwise associate with any other matter that may be found in the sample of interest. The binder can be any analyte-specific receptor material that can be printed onto a substrate and that will specifically bind to an analyte of interest.

Thus, the binder is one part of a specific binding pair with the analyte; examples of analyte/binder pairs include, but are not limited to: antigen/antibody, such as IgE antibody/anti-IgE antibody; antibody/antibody-binding protein (e.g., Protein A or Protein G); enzyme/substrate; oligonucleotide/DNA; chelator/metal; enzyme/inhibitor; bacteria/receptor; bacteria/antibody to bacterial cell markers; or bacteria/anti-CRP antibody; virus/receptor or Influenza A and anti-Influenza A antibodies; fungus/anti-*Aspergillus* antibody; cellular toxin/receptor; cellular toxin/antibody to toxin; fungus/receptor; hormone/receptor; DNA/RNA, or RNA/RNA; oligonucleotide/RNA; and binding of these species to any other species, as well as the interaction of these species with inorganic species. The binder material that is printed onto the substrate is characterized by an ability to specifically bind the analyte or analytes of interest. The variety of materials that can be used as a binder material are limited only by the types of material which will combine selectively (with respect to any chosen sample) with the analyte. Subclasses of materials which can be included in the overall class of receptor materials includes toxins, antibodies, antigens, hormone receptors, parasites, cells, haptens, metabolites, allergens, nucleic acids, nuclear materials, autoantibodies, blood proteins, cellular debris, enzymes, tissue proteins, enzyme substrates, coenzymes, neuron transmitters, viruses, viral particles, microorganisms, proteins, saccharides, chelators, drugs, and any other member of a specific binding pair. This list only incorporates some of the many different materials that can be printed onto the substrate to produce a diagnostic device. Whatever the selected analyte of interest is, the binder is designed to bind, react or otherwise associate with the analyte(s) of interest.

Generally, the binder is printed onto a substrate, for example a plastic film, in a defined pattern such that the binder-printed film does not diffract electromagnetic radiation when the electromagnetic radiation is reflected off of or transmitted through the binder-printed film but diffracts electromagnetic radiation after the binder-printed film is exposed to the analyte and the analyte has bound, reacted or otherwise associated with the binder. Alternatively, the binder-printed film or surface may exhibit a measurable increase or decrease in diffraction after exposure to the analyte. For example, a film may be printed with a binder such that the binder-printed film does not diffract light but does diffract after an analyte binds, associates or otherwise reacts with the binder-printed surface. In another example, the binder-printed film initially diffracts light but does not diffract light or diffracts less after an analyte binds, associates or otherwise reacts with the binder-printed surface. In yet another example, the film may be printed with a binder so that binder-printed film initially diffracts light but when the analyte binds with binder-printed surface, light is diffracted to a measurably greater extent. Thus, the presence of analyte can be determined by a measurable change in diffraction of light that is transmitted through or reflected off of the substrate surface. If light or other electromagnetic radiation is to be transmitted through the surface of a film to detect diffraction, it is desirable that the film is transparent or at least partially transparent to the light or other electromagnetic radiation that will be used to detect diffraction.

Devices of the present invention include a surface or at least a portion of a surface that is printed with a binder. The printing of the surface may be accomplished by microcontact printing the binder onto the surface in a defined pattern. Microcontact printing is desirable and allows printing of patterns with size features of about 100 μm and smaller. Features in this size range are desirable for diffraction when the electromagnetic radiation wavelength is in the spectrum of visible light, from about 4000 Angstroms to 7000 Angstroms. However, it is noted that light over other wavelengths, both longer and shorter wavelength electromagnetic radiation, may be used to detect diffraction. A pattern of binder allows for the controlled attachment of analyte or analyte receptor. An elastomeric stamp may be used to transfer binder to a surface. If the stamp is patterned, a patterned binder layer will be printed on the surface when the stamp is wet with the binder, dried, and then contacted with the surface.

Gold-coated, printed films that produce diffraction patterns and methods of contact printing such films are described and disclosed in U.S. Pat. Nos. 6,020,047 and 6,048,623, which are hereby incorporated by reference herein in their entirety. U.S. Pat. Nos. 6,020,047 and 6,048,623 describe methods of microcontact printing self-assembling monolayers that allow for the selective placement of reagents that can react chemically or physically with an analyte or a group of analytes that are of interest to produce a diffraction image.

Generally, an analyte may be any stimulus including but not limited to any chemical or biological species, compound, composition, moiety, particle, and so forth that that will bind, react or otherwise associate with the binder or with which the binder will respond. Analytes that are contemplated as being detected include, but are not limited to, one or more the following: species of bacteria, including, but not limited to, Hemophilis, *Neisseria meningitides* serogroups A, B, C, Y and W135, *Streptococcus pneumoniae;* yeasts; fungi; viruses including, but not limited to, *Haemophilus influenza* type B or RSV; rheumatoid factors; antibodies including, but not limited to, IgG, IgM, IgA and IgE antibodies; antigens including, but not limited to, streptococcus Group A antigen, streptococcus Group B antigen, viral antigens, fungal antigens, an antigen derived from microorganisms, antigens associated with autoimmune diseases, influenza and tumors; allergens; enzymes; hormones; saccharides; proteins, such as C-reactive protein (CRP); lipids; carbohydrates; drugs including, but not limited to, drugs of abuse and therapeutic drugs, nucleic acids; haptens, environmental agents, other blood-born disease markers; and so forth.

A binder may be microprinted on a polymer film or other substrate. Desirably, a binder is selected and printed that is an analyte-specific receptor material and specifically binds to the analyte or class of analytes of interest. Thus, the binder material and analyte are defined as a specific binding pair with the analyte; examples of analyte/binder pairs include, but are not limited to, antigen/antibody, antibody/antibody-binding protein, enzyme/substrate, oligonucleotide/DNA, chelator/metal, enzyme/inhibitor, bacteria/receptor, virus/receptor, cellular toxin/receptor, fungus/receptor, hormone/receptor, DNA/RNA, or RNA/RNA, oligonucleotide/RNA, and binding of these species to any other species, as well as the interaction of these species with inorganic species. The binder material that is printed on to a substrate layer is characterized by an ability to specifically bind the analyte or analytes of interest. The variety of materials that can be used as a binder material are limited only by the types of material which will combine selectively (with respect to any chosen sample) with the analyte. Subclasses of materials which can be included in the overall class of binder materials include toxins, antibodies, antigens, hormone receptors, parasites, cells, haptens, metabolites, allergens, nucleic acids, nuclear materials, autoantibodies, blood proteins, cellular debris, enzymes, tissue proteins, enzyme substrates, coenzymes, neuron transmitters, viruses, viral particles, microorganisms, proteins, saccharides, chelators, drugs, and any other member of a specific binding pair.

U.S. Pat. No. 6,180,288 and International Publication No. WO 98/43086 disclose and describe the use of one or more responsive gels coated on a patterned self-assembling monolayer and the use of such devices. The responsive gels described therein react or respond to a stimulus, i.e. an analyte, to produce a diffraction image. U.S. Pat. No. 6,180,288 and International Publication No. WO 98/43086 are both hereby incorporated by reference herein in their entirety.

Diffraction-based detectors and methods of detection using optical diffraction that do not require self-assembled monolayers are disclosed and described in U.S. Pat. No. 6,060,256 and International Publication No. WO 99/31486. U.S. Pat. No. 6,060,256 and International Publication No. WO 99/31486 are hereby incorporated by reference herein in their entirety. U.S. Pat. No. 6,060,256 and International Publication No. WO 99/31486 also disclose and describe the optional addition of nutrients for a specific class of microorganisms with such diagnostic devices, systems and methods to provide for the detection of lower concentrations of analytes.

U.S. Pat. No. 6,221,579 and International Publication No. WO 00/34781 disclose and describe the addition of diffraction enhancing elements. Diffraction enhancing element particles that may be used with the present invention include, but are not limited to, glass, cellulose, synthetic polymers or plastics, latex, polystyrene, polycarbonate, bacterial or fungal cells, metallic sols, and so forth. A desirable particle size ranges from a diameter of approximately 0.05 µm to 100.0 µm. The composition of the element particle and structural and spatial configuration of the particle is not critical to the present invention. However, it is desirable that the difference in refractive index between the medium and the enhancing element is between 0.1 and 1.0. Diffraction enhancing elements are optionally included in such devices, systems and methods to provide for the detection of smaller species of analyte, such as proteins, DNA, RNA, other low molecular weight analytes and low molecular weight surface markers on organisms. U.S. Pat. No. 6,221,579 and International Publication No. WO 00/34781 describe the modification of microspheres so that the microspheres are capable of binding with a target analyte and to the device surface. The microspheres are capable of producing a substantial change in height and/or refractive index to enhance diffraction, thereby increasing the efficiency of such devices, systems and methods and can provide for the detection of smaller species of analyte. U.S. Pat. No. 6,221,579 and International Publication No. WO 00/34781 are hereby incorporated by reference herein in their entirety.

International Publication No. WO 00/36416 describes and discloses devices and systems comprising a patterned deposition of antibody-binding proteins for detecting antibodies. International Publication No. WO 00/36416 is also hereby incorporated by reference herein in its entirety.

FIG. 1 is a topside view of the exterior of device 100. In the embodiment illustrated in FIGS. 1-10, the device 100 comprises a housing 20 and a test strip 40. A top view of test strip 40 is illustrated in FIG. 4. To provide a diffraction-based diagnostic test and device, test strip 40 includes a test surface 42 on to which a binder 44 is printed in a defined pattern (not illustrated). Diffraction-based test methods and devices for detecting one or more analytes are described in detail in the above-referenced patents and patent applications. Persons of skill in the art will recognize that other test strips and test methods may be used with the present invention.

FIG. 2, is left side view of device 100. FIG. 3, is a cross-sectional view of device 100 taken through line 3-3 of FIG. 2. In this illustrated embodiment, the device 100 is sealingly attached to a removable test strip 40 to form a first chamber 30 into which a sample can be directed so that sample may contact test strip 40 and test surface 42. The housing 100 further comprises an opening 22 for receiving a sample and a first channel 24 connecting the opening 22 to chamber 30 so that sample may be directed from opening 22 to chamber 30. In another embodiment, the opening 22 may further comprise a collection pad onto which a sample may be placed or otherwise deposited for testing. For example, an individual may contact a freshly lanced finger or other body part to the collection pad to deposit a blood sample for testing within the device 100. The collection pad and opening 22 are in fluid communication and connected to chamber 30 via channel 24. The sample can be directed from the opening 22 to test surface 42 by operating the means for inducing a pressure differential on a sample to direct the sample to a test surface. The means for inducing a pressure differential on a sample to direct the sample to a test surface may be any means that can be used to direct, force, urge or otherwise compel a sample from one location to another location.

In the embodiments illustrated in FIGS. 1-10, the means for inducing a pressure differential on a sample to direct the sample to a test surface is a syringe or a syringe-like device, illustrated generally as 50. Exemplary means for inducing a pressure differential on a sample to direct the sample to a test surface include any device for imparting pneumatic, hydraulic or mechanical pressure on a sample, such as, a syringe, a piston, a pump, a bladder, a vacuum and so forth. The syringe-like device 50 illustrated comprises a piston 52 that is slidingly and sealingly engaged with the inner wall of a second, cylindrical chamber 56. The syringe-like device 50 is operated by either depressing or pulling on handle 54 that is connected to piston 52 to induce a positive or negative pressure differential and push or pull a sample, respectively. In this illustrated embodiment, the means for inducing a pressure differential on a sample to direct the sample to a test surface, the syringe-like device 50, is adapted and arranged to induce a negative pressure differential on a sample and pull the sample from the first chamber 30, through a second channel 26, and into the second chamber 56 as the handle 54 is extended. In at least one particular embodiment, the inner wall of a cylindrical chamber 56 is provided with ridges 58, detents or other means of informing a user of the device that a particular position is reached and notifies the user to stop pulling on the handle for a short period of time so that the device or contents of the device can perform a particular function, such as diluting or filtering or lysing the sample.

The operation of a device of the present invention and a method of performing a diffraction-based diagnostic test will now be described with respect to detecting C-reactive protein (CRP), a biomarker that indicates bacterial infection. Persons of skill in the art will recognize that devices and methods of the present invention can be adapted and modified to perform other types of diagnostic tests, including diagnostic test that are not diffraction based, such as pH tests, lateral flow tests, or color strips, and to detect analytes other than CRP. FIGS. 5, 6 and 7 are cross-sectional views of the diagnostic device taken through line 3-3 of FIG. 2 in various stages of operation of the pressure-assisted means. The position of a liquid sample within the device in the various stages is illustrated by dashed lines.

A health-care professional or a non-professional may use the following described version of the illustrated device to detect CRP in blood and determine if a person from whom a blood sample, or possibly another type of sample, is obtained is suffering from a bacterial infection. With the handle 54 in the unextended position illustrated in FIG. 1, a volume of blood, for example a drop of blood, is contacted to the collection pad and opening 22. Once the sample has contacted the collection pad, handle 54 may be extended to Position 1 as illustrated in FIG. 5. The volume of blood is then drawn from the collection pad, through opening 22 and into channel 24 by the vacuum created when handle 54 is moved from a closed position to Position 1. In FIG. 5, the sample 60 is illustrated entering optional chamber 34. Optional chambers may be included to provide for various functions. For example, chamber 34 may be provided in the device to include a filter for removing one or more undesirable components from a sample, a diluent to lower the viscosity of and thus increase the flow of a sample through the device, or to contain a reactant, an additive or other useful composition. In a desired embodiment, the diagnostic device includes a means for diluting a sample, for example a diluent, in chamber 34. In this desired embodiment, chamber 34 may contain a diluent or any other composition that may be used to dilute, dissolve or otherwise react with one or more components in a sample or to perform another desirable function on a sample so that the sample is affected in some manner that provides more reliable test results for the analyte being tested. Sample 60 contacts the means for diluting a sample via channel 24 when handle 54 is extended to Position 1.

The device may be further provided with yet another optional chamber 36. Chamber 36 may be provided in the device to include a filter for removing one or more undesirable components from a sample, a diluent to lower the viscosity of and thus increase the flow of a sample through the device, or to contain a reactant, an additive or other useful composition. In a further desirable embodiment, the diagnostic device includes a means for separating one or more components from a sample in chamber 36. Examples of means for separating one or more components from a sample include a membrane, filter media, porous films, nonwoven films, paper, etc. Such means for separating one or more components from a sample may be used to remove one or more components from a sample that are undesirable or that may adversely affect testing. For example, it may be desirable to remove red blood cells from a blood sample via filtration, lysing or agglutination. Removal of red blood cells from a sample may improve the function of diagnostic devices and methods because red blood cells may interfere with the analyte binding or otherwise associate with the printed binder; thus, removal could improve test accuracy. The means for separating one or more components from a sample may be general and remove a component or components based on a particular property, for example, size or molecular weight. Or, the means for separating one or more components from a sample may be specific to a particular component, for example a bilirubin-binding layer may be included to remove bilirubin. Sample is further directed through channel 24 and into chamber 36 by extending handle 54 to Position 2. Position 2 is illustrated in FIG. 6. In Position 2, the sample is illustrated as contacting the test surface 42. However, the number of positions may vary and the location of the sample within the device may vary. Once the sample has contacted the test surface 42, handle 54 can be further extended, preferably fully extended, to remove excess sample from the test surface so that the test surface can be read. Advantageously, if the volume of chamber is greater than the volume of blood that is produced from a freshly lanced finger (approximately 25 µL) or greater than the average volume (for example greater than 50 µL or even greater than 100 µL)) the liquid sample can be safely stored before the test strip 40 is removed from the device 100. In a desirable embodiment, test strip 40 is removably attached to the device 10 and can be snapped off of or otherwise removed from the device to be viewed or placed in an analyzer for viewing or interpreting the results.

In another desirable embodiment, the device is provided with windows and/or indicia, for example numbered windows 1, 2 and 3 illustrated in FIG. 8, to assist a user in operating the device. After placing a sample on the touch pad 22, the user pulls handle 54 and aligns piston 52 with Position 1 to pull a sample from the touch pad through channel 24 and into the chamber 34, which includes a means for diluting a sample. Position 1 is illustrated in FIG. 5 and the sample is illustrated as dashed area. The sample may then be allowed to dilute, dissolve or otherwise react with a desired composition in the chamber for a particular period of time. The device may contact one or more compositions in chamber 34 that can be used to modify the sample in some manner. For example, a composition may be provided to reduce the viscosity of the sample, dissolve solids in the sample, or add reactants or diffraction enhancing elements to the sample. Next, the user further pulls handle 54 to align piston 52 with Position 2 to draw the sample further through channel 24, through the chamber 36, which includes a means for separating and into chamber 30. Position 2 is illustrated in FIG. 6. In this described embodiment, the sample has been dissolved in a diluent and one or more desirable components have been removed from the sample before the sample contacts the binder-printed test surface 44. Next, the user further pulls handle 54 to Position 3 to remove excess sample from the test surface. Position 3 is illustrated in FIG. 7. The test strip 40 may now be removed from the device 100 and observed or inserted into a reader to be interpreted.

Although FIGS. 1-10 illustrate a syringe-like device 50 as a means for inducing a pressure differential on a sample, one skilled in the art could configure and construct a device that comprises a means for inducing a pressure differential on a sample that is not a syringe or a syringe-like device. Furthermore, one skilled in the art will appreciate that the devices of the present invention may be configured and constructed to comprise a means for inducing a pressure differential on a sample that uses a positive pressure differential instead of a negative pressure differential to push rather than pull a sample to the test surface. Examples of means for inducing a positive pressure differential include a pump, a plunger, a piston as well as a syringe. The means for inducing a pressure differential may be used to either pull a sample from an opening 22 to a test surface 42 or to push a sample from an opening 22 to a test surface 42 as long as the means directs a sample or a portion of a sample to the test surface so that the sample can be analyzed.

While various patents and other reference materials have been incorporated herein by reference, to the extent there is any inconsistency between incorporated material and that of the written specification, the written specification shall control. In addition, while the invention has been described in detail with respect to various specific examples, illustrations and embodiments thereof, it will be apparent to those skilled in the art that various alterations, modifications and other changes may be made to the invention without departing from the spirit and scope of the present invention. It is therefore intended that the appended claims cover all such modifications, alterations and other changes.

The invention claimed is:

1. A diagnostic device comprising:
a housing comprising i) an opening for receiving a sample, ii) a first chamber into which the sample may be directed, iii) a first channel positioned to provide unreacted sample to the first chamber, and iv) a second channel positioned to remove unreacted sample from the first chamber;
a test strip removably attached to the housing, wherein the test strip defines a test surface in fluid communication with the first chamber so that the sample may be reacted;
a second chamber positioned for receipt of unreacted sample from the first chamber, the second chamber in fluid communication with the second channel;
means for inducing a negative pressure differential on the sample comprising a syringe having a piston that slidingly and sealably engages the second chamber, the means for inducing a negative pressure differential on the sample directs the sample through the first channel, into the first chamber, to the test surface, and thereafter removes an unreacted portion of the sample from the test surface, through the second channel, and into the second chamber; and
a first indicator corresponding to a first piston position that indicates the sample has reached the first chamber and a second indicator, the second indicator corresponding to a second piston position that indicates the sample has reached the second chamber.

2. The diagnostic device of claim 1, wherein the test surface is a diffraction-based test surface.

3. The diagnostic device of claim 2, wherein the device further comprises diffraction-enhancing elements.

4. The diagnostic device of claim 2, wherein the test surface is defined by a polymer film or metal-coated polymer film.

5. The diagnostic device of claim 1, wherein the second chamber has a volume sufficient to contain the entire sample.

6. The diagnostic device of claim 1, further comprising a third chamber positioned for receipt of unreacted sample from the opening, the third chamber located upstream of the first chamber, the third chamber in fluid communication with the first channel; and a third channel, the third channel positioned to provide unreacted sample from the opening to the third chamber.

7. The diagnostic device of claim 6, wherein the third chamber comprises a means for separating one or more components from the sample comprising a filter, membrane, film, nonwoven, paper, precipitating agent, cell lysing agent, or combination thereof.

8. The diagnostic device of claim 7, wherein the means for separating one or more components from the sample removes red blood cells from the sample.

9. The diagnostic device of claim 6, wherein the third chamber comprises a means for diluting the sample comprising a diluent.

10. The diagnostic device of claim 6, wherein the device further comprises a third indicator corresponding to a third piston position that indicates the sample has reached the third chamber.

11. The diagnostic device of claim 1, wherein the test surface is applied with an analyte-specific binder.

12. The diagnostic device of claim 1, wherein the first channel is formed by a capillary tube.

13. The diagnostic device of claim 1, wherein the sample is blood.

* * * * *